United States Patent
Baumgartel

(10) Patent No.: US 10,359,399 B2
(45) Date of Patent: Jul. 23, 2019

(54) METHOD AND DEVICE FOR DETERMINING THE SPATIAL POSITION OF DAMAGE ON A GLASS BODY

(71) Applicant: HELLA GMBH & CO. KGAA, Lippstadt (DE)

(72) Inventor: Klaas Hauke Baumgartel, Delmenhorst (DE)

(73) Assignee: HELLA GMBH & CO. KGAA, Lippstadt (DE)

(*) Notice: Subject to any disclaimer, the term of this patent is extended or adjusted under 35 U.S.C. 154(b) by 322 days.

(21) Appl. No.: 15/069,388

(22) Filed: Mar. 14, 2016

(65) Prior Publication Data

US 2016/0266070 A1 Sep. 15, 2016

(30) Foreign Application Priority Data

Mar. 14, 2015 (DE) .......................... 10 2015 003 341

(51) Int. Cl.
   *G01N 29/07* (2006.01)
   *G01M 17/013* (2006.01)
   *G01N 29/36* (2006.01)

(52) U.S. Cl.
   CPC ........ *G01N 29/075* (2013.01); *G01M 17/013* (2013.01); *G01N 29/36* (2013.01); *G01N 2291/0232* (2013.01); *G01N 2291/0289* (2013.01); *G01N 2291/2698* (2013.01)

(58) Field of Classification Search
   CPC ................. G01N 29/075; G01N 29/36; G01N 2291/0232; G01N 2291/0289; G01M 17/013

USPC ......................................................... 73/598
See application file for complete search history.

(56) References Cited

U.S. PATENT DOCUMENTS

| | | | | |
|---|---|---|---|---|
| 6,153,995 A | * | 11/2000 | Tanaka | B60Q 1/1423 307/10.1 |
| 8,392,486 B2 | * | 3/2013 | Ing | G06F 3/043 708/191 |
| 9,466,085 B2 | * | 10/2016 | Mullen | G06Q 40/08 |
| 2015/0212189 A1 | * | 7/2015 | Kneifel | G01S 3/80 367/125 |

FOREIGN PATENT DOCUMENTS

| | | |
|---|---|---|
| DE | 102004049380 A1 | 4/2006 |
| DE | 102014001258 A1 | 7/2015 |
| EP | 1884414 A1 | 2/2008 |
| SU | 000000930109 A1 | 5/1982 |

* cited by examiner

*Primary Examiner* — Tarun Sinha
(74) *Attorney, Agent, or Firm* — Muncy, Geissler, Olds & Lowe, P.C.

(57) ABSTRACT

In a method for determining the spatial position of damage on a glass body, in particular on a windshield of a vehicle, comprising at least one structure-borne sound sensor and at least one evaluation unit, it is provided according to the invention that the spatial position of a signal source of at least one structure-borne sound signal generated by means of the damage is detected, that the spatial position of the damage is concluded from the spatial position of the signal source, that the spatial position of the damage is checked for spatial overlapping with a predetermined region on the glass body, that this information goes into an information signal in the case of overlapping, and that the information signal is output.

13 Claims, 1 Drawing Sheet

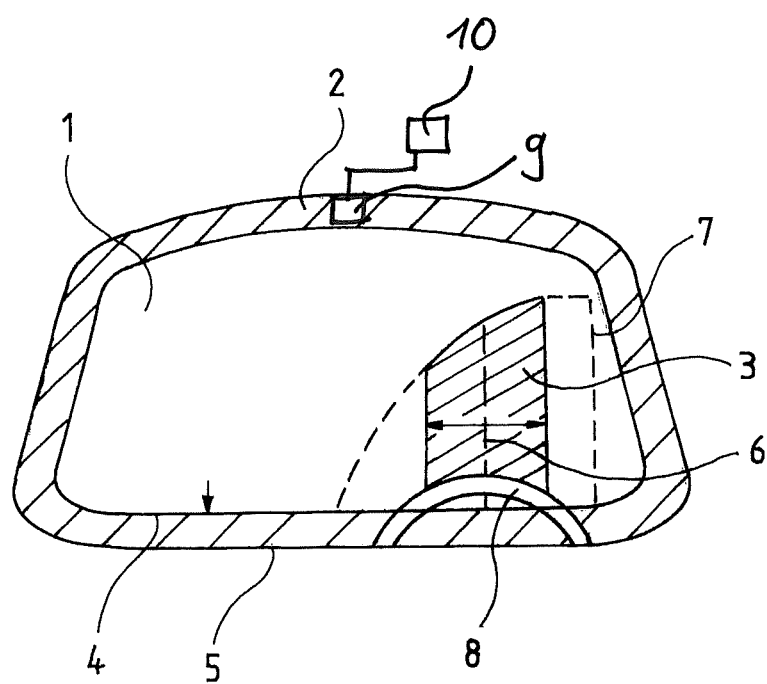

METHOD AND DEVICE FOR DETERMINING THE SPATIAL POSITION OF DAMAGE ON A GLASS BODY

BACKGROUND OF THE INVENTION

Field of the Invention

The invention relates to a method for determining the spatial position of damage on a glass body, in particular on a windshield of a vehicle, comprising at least one structure-borne sound sensor and at least one evaluation unit. The invention further relates to a device for performing the method.

Brief Discussion of the Related Art

Methods and devices for detecting damages are known and used in automobile technology, for example. Specifically, they are used in passenger safety systems, e.g. in the triggering of said systems. For example, DE 10 2004 049 380 A1 describes a vehicle sensor which is provided for detecting vibrations in frequency ranges caused by structure-borne sound, inter alia. Here, the vehicle sensor comprises a processing characteristic for electric signals generated by the detection of different vibrations. The processing characteristic can automatically be set depending on a control signal, wherein the control signal can be an externally generated control signal or a signal generated by the measuring of vibrations generated by the vehicle sensor. The vehicle sensor can for example be used for detecting physical damages such as body damages or glass fraction. The known methods and devices come with the disadvantage that differentiation is not provided as to the region of a glass body, e.g. the windshield of a vehicle, in which the damage has occurred. Information about the spatial position of damage on a windshield is of advantage for the decision as to whether the damage can be repaired by means of a repair method or this is not possible or allowed for safety reasons, for example.

SUMMARY OF THE INVENTION

It is the object of the invention to propose a method and a device for detecting the spatial position of damage on a glass body, in which information about the spatial position of the damage is output.

BRIEF DESCRIPTION OF THE DRAWINGS

In the following, the invention will be described in greater detail by means of a preferred exemplary embodiment illustrated in the drawing. The schematic illustration individually shows in:

The sole FIGURE: a predetermined region on the windshield of a motor vehicle.

DETAILED DESCRIPTION OF THE PREFERRED EMBODIMENTS

In a method for determining the spatial position of damage on a glass body, in particular on a windshield of a vehicle, having at least one structure-borne sound sensor and at least one evaluation unit, it is provided according to the invention that the spatial position of a signal source of at least one structure-borne sound signal generated by the damage is detected, that the spatial position of the damage is concluded from the spatial position of the signal source, that the spatial position of the damage is checked for spatial overlapping with a predetermined region of the glass body and that said information goes into an information signal in the case of spatial overlapping, and that the information signal is output.

As a result of damage on a glass body, e.g. the windshield of a motor vehicle, a structure-borne sound signal is generated on the location of the damage. Starting from the location of the damage, said structure-borne sound signal can propagate radially on the surface of the glass body. By localizing the signal source of the structure-borne sound signal, the location of damage can be determined relative to the position of the structure-borne sound sensor. The position of the signal source, i.e. the position of the damage on the glass body, in particular on the windshield of a vehicle, can be output in the form of an information signal. In particular, an information signal can be output to a vehicle driver indicating the location of the damage on the windshield. Therefore, by means of the information signal, a vehicle user is not only informed on the damage, but also on the location of the damage on the windshield. The information signal can be output by means of an optical signal or an acoustic signal, for example. Besides outputting the information signal to the vehicle passengers, a corresponding information signal can just as well be sent to a vehicle management system, which registers occurring damages, for example, and by means of which respective counter measures can be taken or notifications can be output to the vehicle passengers. The spatial position of the damage can be checked for spatial overlapping with a predetermined region on the glass body. Said predetermined region on the glass body may for example be a predetermined region on windshield of a vehicle, in which region damage poses a particular hazard potential for the vehicle passengers. If a signal source, i.e. damage on the windshield, has been detected, the position of the signal source can be compared to a predetermined spatial region on the windshield. If the damage is located in the predetermined region, this information may go into the information signal. A particular hazard potential may thus be pointed out to a vehicle user or, for example, the information can be stored in a repair management system of a motor vehicle so that said information can be read-out by workshop personnel when visiting a car workshop, for example, and is available as a result. For example, the location of the damage of the windshield can be stored in an error storage or the like so that this information is transmitted upon reading-out said memory.

In a further development of the method, at least one structure-borne sound signal is detected by means of at least three sensor-active elements, the direction under which the structure-borne sound signal encounters the structure-borne sound sensor can be concluded from a time delay of the arrival of the structure-borne sound signal of a certain frequency at the three sensor-active elements, a phase ratio of at least two frequencies of the structure-borne sound signal is detected on at least one sensor-active element, the distance between the signal source and the sensor element is concluded from the phase ratio, and the spatial position of the signal source is concluded from the direction and the distance. The direction from which the structure-borne sound signal encounters the structure-borne sound sensor can be determined independently from the distance between the signal source and the structure-borne sound sensor. For detecting the angle under which the structure-borne sound signal encounters the structure-borne sound sensor, the structure-borne sound sensor may be used with at least two, in particular three sensor-active elements. The structure-borne sound signal arrives at the three sensor-active areas with a time delay. The direction of the arriving sound signal can be concluded from the time delay. Besides the direction under which the damage-generated structure-borne sound signal arrives at the structure-borne sound sensor, the exact localization of the structure-borne sound source requires determining the distance between the structure-borne sound source and the structure-borne sound sensor. The fact that portions of different frequencies of a signal propagate at different speeds on a medium is used for determination of the distance between the structure-borne sound sensor and the signal source. The propagation speeds of the portions of a structure-borne sound wave, in particular of a flexural wave, which typically occur in the case of an impact on a pane, are frequency-dependent. It is a fact that the propagation speed increases along with an increasing frequency. This phenomenon is referred to as dispersion. At the location of the damage, i.e. the location of the signal source, all frequencies of the structure-borne sound signal are excited at the same time and are thus in phase. Due to the frequency-dependent propagation speed, the phase ratio of different frequencies has changed at the location of the structure-borne sound measurement, namely the position of the structure-borne sound sensor. The distance between the signal source and the structure-borne sound sensor can be concluded from said variation. For example, the phase ratio of two frequencies can be determined at the structure-borne sound sensor, so that the distance can be determined accordingly. For example, previously-determined propagation speeds for different frequencies of a structure-borne sound signal on the respective glass body can go into the distance calculation. By means of the calculated distance between the signal source and the structure-borne sound sensor as well as by means of the direction, from which the structure-borne sound signal encounters the sensor, the position of the signal source can be indicated relative to the position of the structure-borne sound sensor.

In a further development of the method, the spatial position of the signal source relative to the position of the structure-borne sound sensor is indicated by polar coordinates. In the method, the distance between the structure-borne signal source and the structure-borne sound sensor as well as the direction in which the structure-borne sounds encounters the structure-borne sound sensor is determined. This allows a particular simple presentation of the spatial position of the structure-borne sound source by means of polar coordinates. By indicating a directional angle and a distance, each point of the region to be monitored can clearly be determined relative to the structure-borne sound sensor. Here, the position of the structure-borne sound sensor serves as the coordinate origin.

In a further development of the method, the predetermined region is a region on a windshield and said region comprises a boundary area which is arranged between the boundary line arranged approximately parallel to the boundary of the windshield and the boundary of the windshield per se. Damage in the boundary area of a windshield poses a particular hazard for the vehicle passengers. If the signal source is located in said boundary area of a windshield, a separate information signal can be output to the vehicle user and/or a vehicle repair management system. Starting from the boundary edges of the windshield, the boundary area may be located between the edges and a boundary line arranged in parallel to the edges of the windshield. Hence, the edge region is configured as a strip on the edge of the windshield. Upon detection of damage between the boundary line and the boundary, i.e. on the edge of the windshield, an information signal is output.

In a further development of the method, the boundary line is arranged at a distance between 5 and 15 cm, in particular 10 cm, to the boundary of the windshield. Thus, the predetermined region particularly comprises a region having a width of 10 cm alongside the boundary, i.e. the edges of the windshield. In said edge region, damages pose a particular hazard source so that in this case, repair, e.g. stone chipping repair, is not possible, or not legally allowed. Said information may be stored in an evaluation unit for the predetermined region, for example, and upon detection of a signal source in the predetermined region, a corresponding information signal including an indication as to the fact that repair is not possible may be output to the vehicle user.

In a further development of the method, the predetermined region on the windshield comprises a region arranged approximately parallel to the sight axis of a driver. The region arranged parallel to the sight axis of a driver corresponds particularly to the sight region of a driver through the windshield. In particular, the driver's sight axis is an imaginary line on the windshield which is arranged perpendicular onto the lower boundary of the windshield at the height of the central axis of the steering wheel. The driver's sight region is limited by the border of the windshield in the downward direction, while an upper boundary may exist in the form of an outer contour of the wiper area of a windshield wiper moving over the windshield. In particular, damage in the sight region arranged in parallel to the sight axis as well as in the edge region of the windshield may constitute a particular hazard potential.

In a further development of the invention, the sight region arranged in parallel to the sight axis of a driver has a width of at least 25 cm and at most 35 cm, in particular a width of 30 cm. For example, repair due to stone chipping may not be allowed for a sight region having a width of 30 cm that is arranged around the sight axis of a driver on a windshield of a vehicle. The sight region of the driver as well as the edge region of the windshield are stored in an evaluation unit as predetermined regions, and upon occurrence of damage in said region, a signal is output to a repair management system, for example, indicating that repair is not possible in said region.

In a further development of the method, the predetermined region is defined as being unrepairable, and an information signal is output to a repair management system in the case of spatial overlapping of the spatial position of the signal source and the predetermined region. The predetermined region on the windshield may be composed of an edge region having a width of 10 cm of the windshield as well as of a driver's sight region located around a driver's sight axis having a width of approx. 30 cm. For safety reasons, damage repair is not allowed in said regions. Repair methods, in particular Smart-Repair methods, which can be used for fixing a flaking in another region of the windshield, for example, cannot be implemented in said predetermined region for safety reasons. If damage is detected in said predetermined region, a signal can be sent to a repair management system after having been evaluated by an evaluation unit. Information on the extent of the damage may also be stored in the repair management system so that in the case of severe damage, a signal can be output to the driver of the vehicle, indicating that the damage on the windshield is to be repaired immediately, in particular that the windshield has to be replaced. Furthermore, it can be possible that the damage be stored in the repair management system and that the stored information is output, for example when visiting a workshop, in particular when reading-out an error storage, thus recommending a sight inspection by the workshop personnel. It may as well be possible that if damage is detected in a region outside the predetermined region, a signal is output to the vehicle user and/or a repair management system, indicating the presence of damage and the fact that said damage can be repaired through Smart-Repair methods, for example.

In a further development of the method, an information signal is output to a service facility located outside the vehicle and the information signal includes information on the spatial position of the damage on the windshield. Upon detection of damage on the windshield, besides outputting an information signal for example to the driver or to a repair management system of the vehicle, a signal can be sent to an external facility. For example, the external service facility can be a facility of the vehicle manufacturer, a data center, a motor vehicle workshop or the like. The information signal may be transmitted to a data center of the vehicle manufacturer, for example, so that the information that indicates the presence of damage in a predetermined region on the windshield where repair is not allowed can be further handed on. For example, the information may be sent in writing to the vehicle owner in order to inform him or her that the damage on the windshield poses a hazard and that said damage has to be repaired immediately. It is possible to also transmit the signal to a specialized workshop, which then contacts the owner of the vehicle, for example.

In a further development of the method, the service facility is a workshop, in particular a motor vehicle workshop. Based on the transmission of the information signal including the information on the presence of damage on the windshield of the vehicle, also stating the region of said damage, a motor vehicle workshop may prepare corresponding repair. An initial sight inspection by the workshop personnel for estimating the damage may be omitted as it has already been clarified by means of said information on the location of the damage if repair of the windshield is possible or replacement of the windshield is required. Respective works can be prepared and respective spare parts can be ordered without prior inspection of the vehicle in the workshop. Thus, prolonged waiting times or additional workshop visits can be avoided.

The invention further relates to a device for performing the method, comprising at least one structure-borne sound sensor and at least one evaluation unit, wherein it is provided according to the invention that the structure-borne sound sensor comprises at least three sensor-active elements. The three sensor-active elements enable determination of a direction from which the structure-borne sound signal encounters the structure-borne sound sensor. The structure-borne sound sensor may e.g. be an arrangement of piezoelectric films attached to the windshield. The structure-borne sound sensor can be connected to an evaluation unit, in which the position of the signal source can be determined accordingly. The device comprises at least one signal output device for outputting an information signal, wherein said device can be configured for outputting an acoustic or optical signal to a vehicle passenger or for transmitting the information signal to an external facility. The transmission of the information signal to an external facility can be ensured via a radio connection, an internet connection or the like.

The sole FIGURE illustrates the windshield 1 of a motor vehicle. A predetermined region is located on the windshield 1, which region is composed of an edge region 2 and a sight region 3. The edge region 2 is arranged between a boundary line 4 and the boundary 5 of the windshield 1. The edge region 2 has a width of approximately 10 cm. The sight region 3 is arranged around a sight axis 6 of the driver. The sight axis 6 is arranged approx. perpendicular to the boundary 5 of the windshield 1 at the height of the center axis of the steering wheel 8 of the vehicle. The sight region 3 is limited downward by the boundary 5 of the windshield 1. The sight region 3 is limited upward by the outer contour of a wiper region 7 of a windshield wiper. In the predetermined region being composed of the edge region 2 and the sight region 3, repairs of the windshield 1, for example for fixing stone chipping by means of Smart-Repair, is not allowed for safety reasons. In the case that a signal source, i.e. damage in the predetermined region, is detected by a structure-borne sound sensor 9 and evaluated by an evaluation unit 10, an information signal can be output, indicating the presence of damage and the fact that said damage is unrepairable. The information signal may also be sent to an external service facility, for example, in particular to a motor vehicle workshop, where corresponding repair measures, e.g. an exchange of the windshield 1, can be prepared.

All features mentioned in the description and in the claims can be combined with the features of the independent claim in any manner. The disclosure of the invention is thus not limited to the claimed or described feature combinations, rather all reasonable feature combinations shall be considered as being disclosed.

The invention claimed is:

1. A method for determining the spatial position of damage on a glass body, in particular on a windshield of a vehicle, comprising at least one structure-borne sound sensor and at least one evaluation unit, the method comprising:
    said damage creating a signal source for generating a sound signal at a same spatial position as said damage, a propagation speed of the sound signal being frequency dependent;
    said structure-borne sound sensor detecting said sound signal and generating an output signal;
    storing a predetermined region on the glass body in the evaluation unit;
    said evaluation unit receiving said output signal and determining the distance and direction of the signal source from structure-borne sound sensor based on the frequency and phase of the detected sound signal and predetermined propagation speeds for various frequencies in glass, the spatial position of the signal source and thereby the spatial position of the damage being determined;
    the evaluation unit comparing the spatial position of the damage with the predetermined region on the glass body, to determine spatial overlapping between the damage and the predetermined region;
    the evaluation unit generating an information signal based on the spatial overlapping, and
    the evaluation unit outputting the information signal as a display to the operator of the vehicle and electronically storing the information signal in error storage on the vehicle.

2. The method according to claim 1, wherein the structure-borne sound sensor includes three sensor-active elements, at least one sound signal is detected by at least three sensor-active elements, the direction under which the sound signal encounters the structure-borne sound sensor is concluded from a time delay of the arrival of the sound signal of a certain frequency at the at least three sensor-active elements, a phase ratio of at least two frequencies of the sound signal is detected on at least one sensor-active element, the distance between the signal source and the sensor element is concluded from the phase ratio, and the spatial position of the signal source is concluded from the direction and the distance.

3. The method according to claim 1, wherein the spatial position of the signal source in relation to the position of the structure-borne sound sensor is presented in polar coordinates.

4. The method according to claim 1, wherein the predetermined region is a region on a windshield and the region comprises an edge region which is arranged between a boundary line arranged approximately parallel to the boundary of the windshield and the boundary of the windshield.

5. The method according to claim 4, wherein the boundary line is arranged at a distance between 5 cm and 15 cm, in particular 10 cm, to the boundary of the windshield.

6. The method according to claim 4, wherein the predetermined region on the windshield comprises a sight region arranged approximately parallel to the sight axis of a driver.

7. The method according to claim 6, wherein the sight region arranged parallel to the sight axis of a driver has a width of at least 25 cm and at most 35 cm, in particular of 30 cm.

8. The method according to claim 4, wherein the predetermined region is defined to be unrepairable and an information signal is output to a repair management system in the case of spatial overlapping of the spatial position of the signal source and the predetermined region.

9. The method according to claim 8, wherein an information signal is output to a service facility located outside the vehicle and the information signal includes information about the spatial position of damage on the windshield (1).

10. The method according to claim 9, wherein the service facility is a workshop, in particular a motor vehicle workshop.

11. A device for performing a method according to claim 1, comprising at least one structure-borne sound sensor, at least one evaluation unit and at least one signal output unit, wherein the structure-borne sound sensor comprises at least three sensor-active elements.

12. A method for determining the spatial position of damage on a glass body, in particular on a windshield of a vehicle, comprising at least one structure-borne sound sensor and at least one evaluation unit,
    wherein the spatial position of a signal source of at least one structure-borne sound signal generated by means of the damage is detected by the sound sensor,
    a predetermined region of the windshield is stored in the evaluation unit;
    the spatial position of the damage is concluded by the evaluation unit from the spatial position of the signal source, a propagation speed of the sound signal being frequency dependent,
    the spatial position of the damage is checked for spatial overlapping with a predetermined region on the glass body by the evaluation unit,
    said information goes into an information signal in the case of spatial overlapping, and
    the information signal is output by the evaluation unit and stored in error storage on the vehicle;
        wherein at least one structure-borne sound signal is detected by at least three sensor-active elements, the direction under which the structure-borne sound signal encounters the structure-borne sound sensor is concluded from a time delay of the arrival of the structure-borne sound signal of a certain frequency at the at least three sensor-active elements, and predetermined propagation speeds for various frequencies in glass, a phase ratio of at least two frequencies of the structure-borne sound signal is detected on at least one sensor-active element, the distance between the signal source and the sensor element is concluded from the phase ratio, and the spatial position of the signal source is concluded from the direction and the distance;
        wherein the predetermined region is a region on a windshield and the region comprises an edge region which is arranged between a boundary line arranged approximately parallel to the boundary of the windshield and the boundary of the windshield.

13. The method according to claim 1, wherein the sound sensor is an arrangement of piezoelectric film.

* * * * *